United States Patent
Anderson

(10) Patent No.: US 6,340,477 B1
(45) Date of Patent: Jan. 22, 2002

(54) BONE MATRIX COMPOSITION AND METHODS FOR MAKING AND USING SAME

(75) Inventor: Billy G. Anderson, Virginia Beach, VA (US)

(73) Assignee: LifeNet, Va Beach, VA (US)

( * ) Notice: Subject to any disclaimer, the term of this patent is extended or adjusted under 35 U.S.C. 154(b) by 0 days.

(21) Appl. No.: 09/559,281

(22) Filed: Apr. 27, 2000

(51) Int. Cl.[7] .................... A61K 9/14; A61K 35/32; A61F 2/00; A61F 13/00

(52) U.S. Cl. .............. 424/488; 424/423; 424/422; 424/549

(58) Field of Search ................. 424/488, 422, 424/423, 549

(56) References Cited

U.S. PATENT DOCUMENTS 5,284,655 A * 2/1994 Bogdansky et al. ........ 424/422

* cited by examiner

*Primary Examiner*—Thurman K. Page
*Assistant Examiner*—Blessing Fubara
(74) *Attorney, Agent, or Firm*—Susanne M. Hopkins

(57) ABSTRACT

The invention is directed to a bone matrix composition for use in the repair and healing of osseous tissue. The composition can be used in load-bearing and non-load bearing applications, including for example, orthopaedic applications including spinal applications, and oral-facial applications including dental applications. The composition includes one or more non-liquid semi-synthetic polymers; and particulate bone including allogenic, autogenic, or xenogenic bone, where the bone is cancellous, corticocancellous bone, and/or cortical bone. The composition may also optionally contain one or more pharmaceutically active agents. The composition can be formulated as a gel, putty, a paste, a cake, or solid.

44 Claims, No Drawings

BONE MATRIX COMPOSITION AND METHODS FOR MAKING AND USING SAME

FIELD OF THE INVENTION

The invention is directed to a composition for use in the repair and healing of osseous tissue. The composition contains particulate bone including allogenic, autogenic, or xenogenic bone; cancellous, corticocancellous, and/or cortical bone; and one or more semi-synthetic polymers including for example one or more cellulosics. The composition may also optionally contain one or more pharmaceutically active agents. The composition can be formulated as a gel, putty, paste, cake, or solid.

BACKGROUND OF THE INVENTION

The use of bone material derived from demineralized allogenic or xenogenic bone in surgical repair of bone defects, is known. Bone material contains substances for example, bone morphogenic protein, which induce bone regeneration at a defect site. U.S. Pat. Nos. 5,405,390; 5,314,476; 5,284,655; 5,510,396; 4,394,370; and 4,472,840, disclose compositions containing demineralized bone powder. These prior art compositions are problematic in that they are difficult to handle during surgery or implantation; and wash away during lavage (i.e. does not remain at the implant site). The inventive composition exhibits excellent properties, does not wash away during surgical lavage; and can be formulated as a gel, a putty, paste, or solid, depending on the characteristics desired for the particular application.

SUMMARY OF THE INVENTION

The invention is directed to a bone matrix composition, including bone and one or more semi-synthetic polymers.

The invention is directed to a bone matrix composition where the one or more semi-synthetic polymers include one or more water soluble semi-synthetic polymers.

The invention is yet further directed to a bone matrix composition where the bone is allogenic bone, autogenic bone, or xenogenic bone.

The invention is directed to a bone matrix composition where the one or more semi-synthetic polymers are non-liquid.

The invention is also directed to a bone matrix composition where the composition is in the form of a gel, a putty, a paste, a cake, or a solid.

The invention is directed to a bone matrix composition, including one or more of the following: ground demineralized bone, ground mineralized bone, and ground partially mineralized bone, and one or more semi-synthetic polymers.

The invention is further directed to a bone matrix composition, including one or more of the following: ground demineralized bone, ground mineralized bone, and ground partially mineralized bone, with the bone present in an amount of from 10 wt % to about 85 wt %, preferably from about 20 wt % to about 75 wt %, and more preferably from about 30 wt % to about 70 wt %, and most preferably, from about 35 wt % to about 70 wt %, and including one or more semi-synthetic polymers.

The invention is also directed to a bone matrix composition where the composition is a gel, and the gel includes from about 15 wt % ground demineralized bone to about less than 60 wt % ground demineralized bone.

The invention is also directed to a bone matrix composition where the composition is a putty, and the putty includes from about 30 wt % ground demineralized bone to about 80 wt % ground demineralized bone.

The invention is further directed to a bone matrix composition, including ground, demineralized, xenograft bone and one or more semi-synthetic polymers.

The invention is directed to a bone matrix composition where the composition is a gel, which includes ground demineralized bone present in an amount of from 15 wt % to about less than 60 wt % and one or more cellulosics.

The invention is also directed to a bone matrix composition including one or more plasticizers.

The invention is also directed to a reconstructed bone graft including a bone matrix composition containing demineralized and/or partially demineralized bone and one or more semi-synthetic polymers, which composition has been remineralized.

The invention is directed to a bone matrix composition where the bone is demineralized and/or mineralized and/or partially demineralized cancellous bone.

The invention is directed to a bone matrix composition where the bone is demineralized and/or mineralized and/or partially demineralized, cancellous bone and/or cortical bone and/or corticocancellous bone.

The invention is also directed to a composition including demineralized cortical bone and one or more semi-synthetic polymers, in a gel, a putty, a paste, a cake, or a solid formulation.

The invention is further directed to a bone matrix composition where the cellulosic and/or semi-synthetic polymer, are non-liquid.

The invention is further directed to a composition including demineralized cancellous bone and one or more semi-synthetic polymers in a gel, a putty, a paste, a cake, or a solid formulation.

The invention is directed to a composition including mineralized cancellous bone and one or more semi-synthetic polymers in a gel, a putty, a paste, a cake, or a solid formulation.

The invention is directed to a composition including mineralized cortical bone and one or more semi-synthetic polymers in a putty, a gel, a putty, a paste, a cake, or a solid formulation.

The invention is directed to a composition including surface demineralized cortical bone and one or more semi-synthetic polymers, in a gel, a putty, a paste, a cake, or a solid formulation.

The invention is directed to a composition including demineralized cancellous bone and cortical bone (mineralized and/or demineralized and/or partially demineralized and/or surface demineralized) and one or more semi-synthetic polymers in a gel, a putty, a paste, a cake, or a solid formulation.

The invention is also directed to a composition including partially demineralized cortical bone and one or more semi-synthetic polymers in a gel, a putty, a paste, a cake, or a solid formulation.

The invention is further directed to a composition including partially demineralized cancellous bone and one or more semi-synthetic polymers in a gel, a putty, a paste, a cake, or a solid formulation.

The invention is directed to a composition including partially demineralized cortical bone and partially demineralized cancellous bone and one or more semi-synthetic polymers in a gel, a putty, a paste, a cake, or a solid formulation.

The invention is directed to a composition including partially demineralized cortical and/or cancellous bone; and mineralized and/or demineralized, cortical and/or cancellous bone; and one or more semi-synthetic polymers; in a gel, a putty, a paste, a cake, or a solid formulation.

The invention is further directed to a method for making a bone matrix composition including the steps of mixing bone with one or more dry semi-synthetic polymers to form a dry mixture; and adding water to the dry mixture to form a gelled composition.

The invention is further directed to a method for making a solid composition including the steps of mixing bone with one or more non-liquid semi-synthetic polymers to form a dry mixture; adding water to the dry mixture to form a gelled composition; and removing moisture from the gelled composition, for example using freeze-drying and/or subjecting the gelled composition to negative pressure or positive pressure, to form a solid composition.

The invention is also directed to a method for making a solid composition including the step of subjecting the gelled composition to positive pressure or negative pressure.

The invention is also directed to a method for making a solid composition where moisture is removed from the gelled composition by freeze drying the gelled composition.

The invention is also directed to a method for making a bone matrix composition, where the composition is produced under sterile conditions.

The invention is directed to a method for making a bone matrix composition, including sterilizing the composition produced using radiation.

The invention is directed to a bone matrix composition where one or more water soluble semi-synthetic polymers include one or more cellulosics.

The invention is further directed to a bone matrix composition where the one or more cellulosics include one or more of the following: carboxy methyl cellulose; hydroxy propyl cellulose; hydroxy ethyl cellulose; and methyl cellulose.

DETAILED DESCRIPTION OF THE INVENTION

I. Definitions

The below definitions serve to provide a clear and consistent understanding of the specification and claims, including the scope to be given such terms.

Allogenic. By the term "allogenic" is intended tissue including bone tissue having a different gene constitution than the intended recipient, but being from the same species.

Autogenic. By the term "autogenic" is intended tissue including bone tissue from the intended recipients own body.

Biocompatible. By the term "biocompatible" is intended for the purposes of the invention, any material which does not provoke an adverse response in a patient. For example, a suitable biocompatible material when introduced into a patient does not itself provoke a significant immune response, and is not toxic to the patient.

Bone. By the term "bone" is intended any bone including allograft bone, autograft bone and xenograft bone, and includes bone in any form including but not limited to: mineralized and/or demineralized bone and/or partially demineralized bone, and cancellous and/or cortical bone and/or corticocancellous, where the bone is in a form including but not limited to: particulate bone, ground bone including but not limited to bone in the particle size range of $125\mu$ to about $1000\mu$, preferably about $250\mu$ to $710\mu$, bone chips, cut bone pieces including cubes, iliac crest wedges, Cloward dowels, or strips, and essentially intact bone including the patient's own bone in the patients body, and bone including for example: the femur, tibia, ilia, humorous, radius, ulna, ribs, whole vertebrae, mandibula, and any segment thereof.

Bone defect site. By the term "bone defect site" is intended for the purposes of the invention, any site in an animal including a human, where the inducement of bone growth and/or repair, is desired.

Carboxy methyl cellulose. (CMC) By the term "carboxy methyl cellulose" is intended a semi-synthetic polymer which is water soluble, and is an acid ether derivative of cellulose, where carboxy methyl groups are substituted on the glucose units of the cellulose chain through an ether linkage ( carboxy methyl groups are substituted for the hydroxyl groups along the carbon chain).

Cellulosic. By the term "cellulosic" is intended for the purposes of the invention, any semi-synthetic polymer that is a derivative of cellulose, including but not limited to: methyl cellulose; carboxy methyl cellulose; hydroxy propyl cellulose; and hydroxy ethyl cellulose.

Demineralized Bone. By the term "demineralized bone" is intended for the purposes of this invention, any bone including cortical and/or cancellous bone, from any source including autogenic, allogenic and/or xenogenic bone, demineralized to contain less than about 5 wt % residual calcium.

Dry Bone. By the term "dry" or "dried" bone is intended particulate bone that has been freeze dried or air dried and has a density of about 0.443.

Essentially Free From. By the term "essentially free from" is intended bone where the material removed (i.e., bone marrow, viral, fungal, and/or bacterial particles) from the bone is not detectable using detection means known in the art to which the invention pertains at the time of filing of this application.

Ether Derivative of a Polysaccharide. By the term "ether derivative of a polysaccharide" is intended those derivatives that are also semi-synthetic polymers, and includes acid ether derivatives of polysaccharides including for example, cellulosics including for example, methyl cellulose, carboxy methyl cellulose, hydroxy propyl cellulose, and hydroxy ethyl cellulose.

Flowable. By the term "flowable" is intended a deformable and shape sustaining composition that includes a gel, putty, paste, solid, and a cake.

Gel. By the term "gel" is intended for the purposes of the invention a hydrogel which is a colloid in which the particles are in the external or dispersion phase and water in the internal or dispersed phase. A gel is an intermediate form of matter between a liquid and a solid. The present gels are sufficiently viscous to be extruded through a syringe, and are shape-sustaining and deformable. The gel contains less than 60 wt % bone; and preferably contains about 20 wt % bone to about 65 wt % bone; more preferably from about 25 wt % bone to about 60 wt % bone; even more preferably from about 30 wt % bone to about 55 wt % bone; and most preferably from about 45 wt % to about 49 wt %. Preferably the bone used is demineralized cortical and /or cancellous bone, and is autogenic, allogenic and/or xenogenic bone.

Osteoconductive. By the term "osteoconductive" is intended for the purposes of the invention, the ability of a substance to support or conduct bone growth.

Osteoinductive. By the term "osteoinductive" is intended for the purposes of the invention, the ability of a substance to induce bone growth.

Patient. By the term "patient" is intended for the purposes of the invention, an animal including a human, who is subject to medical treatment.

Partially Demineralized Bone. By the term "partially demineralized bone" is intended, any bone including cortical and/or cancellous bone, from any source including autogenic, allogenic and/or xenogenic bone, demineralized to contain less residual calcium than is present in intact natural bone (that is, demineralized to contain less than about 30 wt % residual calcium) and preferably demineralized to contain more than about 5 wt % residual calcium and less than about 30 wt % residual calcium.

Pharmaceutically Active Agent. By the term "pharmaceutically active agent" is intended, any medically useful substance including any therapeutically beneficial substance, including but not limited to: viricides; microbicides; antibiotics; amino acids; peptides; vitamins; co-factors for protein synthesis; hormones including growth hormones; endocrine tissue; living cells including for example: stem cells, chondrocytes, bone marrow cells, and parenchymal cells; synthesizers; enzymes; angiogenic drugs including nicotine and nicotinic acid; biocompatible surface active agents; antigenic agents; cytoskeletal agents; growth factors including but not limited to: transforming growth factor, and insulin like growth factor; antitumor agents; immunosuppressants; and permeation enhancers.

Plasticizer. By the term "plasticizer" is intended for the purposes of the invention, any biocompatible compounds which are soluble in water and can easily displace/replace water at the molecular level and preferably have a low molecular weight such that the plasticizer fits into the spaces available to water within the hydrated molecular structure of the bone or soft tissue. Suitable plasticizers for use in the invention include but are not limited to: polar and non-polar plasticizers including but not limited to: mono-di or -tri esters of citric acid, phthalic acid, sebacic acid, azaleic acid, adipic acid, trimeilitic acid, and epoxidized soya oils; glycerol; adonitol; sorbitol; ribitol; galactitol; D-galactose; 1,3-dihydroxypropanol; ethylene glycol; tirethylene glycol; propylene glycol; glucose; sucrose; mannitol; xylitol; meso-erythritol; adipic acid; proline; hydroxyproline or similar water-soluble small molecular weight solutes Plasticizers are preferred for use at concentration in the range of from 0.1M to 3.0M and in an amount of from 3.0 to 50.0 wt %, preferably 20.0 to 40.0 wt %, and most preferably about 35.0 wt % to about 40 wt %.

Polysaccharide. By the term "polysaccharide" is intended for the purposes of the invention, any combination of nine or more monosaccharides, linked together by glycosidic bonds.

Putty Composition. By the term "putty composition" is intended for the purposes of the invention a hydrogel which is a colloid in which the particles are in the external or dispersion phase and water in the internal or dispersed phase. The present putty's are moldable and shape sustaining. The putty contains greater than 30 wt %, preferably contains about 40 wt % bone to about 50 wt % bone; more preferably from about 45 wt % bone to about 49 wt % bone; and even more preferably from about 44 wt % to about 48 wt % bone. Preferably the bone used is demineralized cortical and/or cancellous bone, and is autogenic, allogenic and/or xenogenic bone.

Semi-synthetic polymer. By the term "semi-synthetic polymer, is intended any polymer which is preferably water soluble of the semi-synthetic type, and being a macromolecule formed by the chemical union of five or more identical combining units called monomers, and includes chemically treated natural polymers including but not limited to: cellulosics including for example rayon, methyl cellulose, carboxy methyl cellulose, hydroxy propyl cellulose, hydroxy ethyl cellulose, cellulose acetate, and other cellulose ethers; and modified starches including for example acetates and ethers including for example, starch acetate. Water-soluble ethers are preferred semi-synthetic polymers. Less water-soluble semi-synthetic polymers may also be used, for example with a biocompatible solvent that is miscible in water. Such polymers include cellulose plastics including for example cellulose acetate phthalate.

Thixotropic Agent. By the term "thixotropic agent" is intended any substance pertaining to or characterized by thixotropy. Thixotropy is a reclotting phenomenon; it is the property of certain gels of becoming less viscous when shaken or subjected to shearing forces and returning to the original viscosity upon standing; a characteristic of a system exhibiting a decrease in viscosity with an increase in the rate of shear, usually a function of time. Suitable thixotropic agents for use in the invention include but are not limited to the following: carboxyl methyl cellulose; pectin; and methyl cellulose.

Wet bone. By the term "wet bone" is intended bone that is wet; damp; or freeze-dried, wet, and then centrifuged; and such bone has a density of about 0.828.

Xenogenic. By the term "xenogenic" is intended for the purposes of this invention, tissue including bone tissue that is heterologous, with respect to the intended recipient, i.e. the donor and recipient are from widely separated species. For example, if the intended recipient is human, xenogenic tissue would be tissue from a species other than human.

II. The Composition

The invention is a bone matrix composition that contains bone and one or more semi-synthetic polymers. The composition can be formulated as a gel, a putty, a paste, a cake or a solid composition.

Preferred formulations of the inventive composition include: (a) a composition including demineralized cortical bone and one or more semi-synthetic polymers in a putty, gel, paste, cake or solid formulation; (b) a composition including demineralized cancellous bone and one or more semi-synthetic polymers in a putty, gel, paste, cake or solid formulation; (c) a composition including demineralized cancellous and demineralized cortical bone, and one or more semi-synthetic polymers in a putty, gel, paste, cake or solid formulation; (d) a composition including partially demineralized cortical bone and one or more semi-synthetic polymers in a putty, gel, paste, cake or solid formulation; (e) a composition including partially demineralized cancellous bone and one or more semi-synthetic polymers in a putty, gel, paste, cake or solid formulation; (f) a composition including partially demineralized cortical bone and partially demineralized cancellous bone and one or more semi-synthetic polymers in a putty, gel, paste, cake or solid formulation; and (g) a composition including partially demineralized cortical and/or cancellous bone, and mineralized and/or demineralized, cortical and/or cancellous bone, and one or more semi-synthetic polymers in a putty, gel, paste, cake or solid formulation.

Preferred semi-synthetic polymers include water-soluble semi-synthetic polymers. Preferred water-soluble, semi-synthetic polymers include cellulosics. Preferred cellulosics include methyl cellulose; carboxy methyl cellulose; hydroxy ethyl cellulose; and hydroxy propyl cellulose.

Preferred formulations of the inventive gel, include: one or more semi-synthetic polymers in an amount of from 0.5 wt % to about 4.0 wt %, preferably from about 1.0 wt % to about 3.5 wt %, more preferably from about 1.5 wt % to about 3.2 wt %, and most preferably from about 2.0 wt % to about 2.9 wt %. The use of demineralized bone is preferred and is present in an amount of from 30.0 to 55.0 wt %, preferably from about 40.0 wt % to about 50.0 wt %, more preferably from about 45.0 wt % to about 49.0 wt %, and most preferably about 47.0 wt %. Water is present in an amount of from about 40.0 wt % to about 60.0 wt %, preferably from about 45.0 wt % to about 55.0 wt %, most preferably from about 48.0 wt % to about 53.0 wt %, and most preferably about 51.0 wt %. Specific preferred gel formulations include formulations containing from about 2.0 wt % to about 2.9 wt % of a cellulosic, preferably carboxy methyl cellulose; about 47.0 wt % demineralized bone; and about 51.0 wt % water.

Preferred formulations of the inventive paste, include: one or more semi-synthetic polymers in an amount of from 2.5 wt % to about 6.0 wt %, preferably from about 3.0 wt % to about 4.5 wt %, more preferably from about 3.4 wt % to about 4.2 wt %, and most preferably about 3.8 wt %. The use of demineralized bone is preferred and is present in an amount of from 30.0 to 55.0 wt %, preferably from about 40.0 wt % to about 50.0 wt %, more preferably from about 45.0 wt % to about 49.0 wt %, and most preferably about 47.0 wt %. Water is present in an amount of from about 40.0 wt % to about 60.0 wt %, preferably from about 45.0 wt % to about 55.0 wt %, most preferably from about 48.0 wt % to about 52.0 wt %, and most preferably about 50.0 wt %. Specific preferred paste formulations include formulations containing about 3.8 wt % of a cellulosic, preferably carboxy methyl cellulose; about 47.0 wt % demineralized bone; and about 50.0 wt % water.

Preferred formulations of the inventive putty, include: one or more semi-synthetic polymers in an amount of from 6.0 wt % to about 13.0 wt %, preferably from about 7.0 wt % to about 12.0 wt %, more preferably from about 7.5 wt % to about 11.0 wt %, and most preferably from about 8.0 wt % to about 9.7 wt %. The use of demineralized bone is preferred and is present in an amount of from 30.0 to 55.0 wt %, preferably from about 40.0 wt % to about 50.0 wt %, more preferably from about 45.0 wt % to about 49.0 wt %, and most preferably about 44.0 wt % to about 48.0 wt %. Water is present in an amount of from about 35.0 wt % to about 55.0 wt %, preferably from about 40.0 wt % to about 50.0 wt %, most preferably from about 42.0 wt % to about 48.0 wt %, and most preferably from about 44.0 wt % to about 46.0 wt %. Specific preferred putty formulations include formulations containing from about 8.0 wt % to about 9.7 wt % of a cellulosic, preferably carboxy methyl cellulose; from about 44.0 wt % to about 48.0 wt % demineralized bone; and from about 44.0 wt % to about 46.0 wt % water.

Preferred formulations of the inventive cake, include: one or more semi-synthetic polymers in an amount of from 8.0 wt % to about 16.0 wt %, preferably from about 9.0 wt % to about 15.0 wt %, more preferably from about 10.0 wt % to about 14.0 wt %, and most preferably about 12.0 wt %. The use of demineralized bone is preferred and is present in an amount of from 60.0 to 90.0 wt %, preferably from about 65.0 wt % to about 85.0 wt %, more preferably from about 70.0 wt % to about 80.0 wt %, and most preferably about 75.0 wt %. Water is present in an amount of from about 5.0 wt % to about 21.0 wt %, preferably from about 8.0 wt % to about 19.0 wt %, most preferably from about 10.0 wt % to about 15.0 wt %, and most preferably about 13.0 wt %. Specific preferred cake formulations include formulations containing about 12.0 wt % of a cellulosic, preferably carboxy methyl cellulose; about 75.0 wt % demineralized bone; and about 13.0 wt % water.

The above recited weight percent amounts reported for "bone" are based on wet centrifuged bone having a density of about 0.828. The weight percent for damp or dry bone can be calculated based on the density of the damp or dry bone samples, and such calculation can be readily performed by one of ordinary skill in the art without undue experimentation.

III. Methods of Making the Bone Matrix Composition

The inventive composition including a gel, putty, paste, cake, and solid formulations are all initially prepared by first combining the non-liquid semi-synthetic polymer with the bone which bone is preferably demineralized bone in a particulate form where the bone is dry or wet. Thereafter, the non-liquid particulate bone/polymer combination is mixed with water to form a bone matrix composition. Preparation of the composition may be carried out sterilely or the composition may be sterilized after packaging using irradiation, for example e-beam sterilization.

The composition may optionally contain one or more additional substances including but not limited to: one or more thixotropic agents, one or more plasticizers, one or more therapeutically beneficial substances and/or pharmaceutically active substances, including but not limited to growth factors including bone growth factors including for example bone morphogenic protein. Suitable bone material includes freeze-dried bone, air-dried bone; and/or wet bone including for example wet centrifuged bone, where the residual moisture content of the bone is preferably less than 8.0 %, more preferably less than 7.0 % and most preferably less than 6.0 % residual moisture. The bone material is preferably particulate bone. Suitable bone material includes demineralized bone, and/or partially demineralized bone, and/or mineralized bone, where the bone is cortical bone, and/or corticocancellous bone, and/or cancellous bone.

Optional substances including any one or more of a pharmaceutically active agent, a therapeutically beneficial substance, a thixotropic agent, and a plasticizer, may be added to the composition before, during, or after, the addition of bone to the non-liquid particulate mixture of bone and polymer.

The composition may be packaged and sterilized for example using irradiation, and distributed. For example, the gel formulation may be sterilely packaged in a syringe, and the putty, paste, cake, or solid, formulation may be sterilely packaged in a jar or blister package, and then sterilized.

IV. Use of the Bone Matrix Composition

The compositions are useful for repairing bone defects arising from any cause including congenital defects and trauma induced defects.

The compositions are suitable for use in dental applications, neurosurgical, and orthopaedic applications, as well as in any application where the repair of a bone defect, including a bone void, is desired.

Further details of the process and products of the invention are presented in the examples that follow:

EXAMPLES

I. Putty and Gel Formulations of the Bone Matrix Composition

Various formulations of the present composition were produced and graded at zero aging (graded as soon as the composition was produced) based on a scale of from 1.0 to 10.0 with 1.0 being poor and 10.0 being excellent. Grading was based on handling characteristics, wash-away characteristics, stickiness, uniformity, ability to form a ball, and flowability in the case of a gel, moldability in the case of a paste. Desired qualities exhibited by a putty include the ability to form a ball, no stickiness, moldability, uniformity, the ability to stay intact in the presence of water, deformability and the ability to sustain its shape. Desired qualities exhibited by a gel include extrudability, uniformity, deformability, the ability to sustain its shape, and no stickiness. The formulations and results are set forth below in Table 1.

Sample formulation A was produced by mixing the CMC with water, and then adding the particulate bone to the water/CMC mixture. The resultant putty was of poor quality in that it was dry and crumbly, would not form a ball, and was not moldable. The remaining samples B–I, were produced by mixing damp particulate demineralized cortical bone with dry carboxy methyl cellulose (CMC), and then combining the mixture with water to form the composition. The formulation samples were then graded.

TABLE 1

| Sample | wt % damp bone | wt % dry CMC | wt % water | grade | gel/putty |
|---|---|---|---|---|---|
| A | 44.3 | 8.5 | 47.2 | 2.0 | putty |
| B | 40.0 | 9.7 | 50.3 | 9.0 | putty |
| C | 59.0 | 16.9 | 23.9 | 8.0 | putty |
| D | 51.2 | 19.5 | 29.3 | 6.0 | putty |
| E | 44.4 | 9.7 | 45.9 | 9.5 | putty |
| F | 43.7 | 5.0 | 51.3 | 5.0 | putty |
| G | 47.9 | 8.0 | 44.1 | 9.6 | putty |
| H | 47.1 | 2.0 | 50.8 | 8.0 | gel |
| I | 46.6 | 2.9 | 50.5 | 8.5 | gel |

II. Osteoinductivity of Gel and Putty Compositions

The osteoinductivity of a preferred gel formulation of the composition containing: 2.0 wt % CMC, 47.0 wt % demineralized cortical bone, and 51.0 wt % water, was compared to the osteoinductivity of a control containing only demineralized cortical bone. Eight samples of each of the composition and the control were implanted into nude mice. At 28 days the mice were sacrificed and the degree of remineralization of each implant was determined.

The percent remineralization of the control demineralized bone was 5.1±0.7 %. The percent remineralization of the composition was 4.2±0.9 %. The difference between the remineralization of the control and the composition was not statistically significant, p=0.1051. In conclusion, the composition is statistically as as the "gold standard", ie. the demineralized bone control.

All of the publications cited herein are hereby incorporated by reference in their entirety, into the present disclosure. It will be appreciated by those skilled in the art that various modifications can be made without departing from the essential nature thereof. It is intended to encompass all such modifications within the scope of the appended claims.

I claim:

1. A bone matrix composition, consisting essentially of: one or more non-liquid members selected from the group consisting of: methyl cellulose, carboxy methyl cellulose, hydroxy propyl cellulose, and hydroxy ethyl cellulose; particulate bone; and water.

2. A bone matrix composition, consisting essentially of: one or more non-liquid members selected from the group consisting of: methyl cellulose, carboxy methyl cellulose, hydroxy propyl cellulose, and hydroxy ethyl cellulose; particulate bone; water; and one or more pharmaceutically active agents.

3. A bone matrix composition, consisting essentially of: one or more non-liquid members selected from the group consisting of: methyl cellulose, carboxy methyl cellulose, hydroxy propyl cellulose, and hydroxy ethyl cellulose, in an amount of from about 0.1 wt % to about 9.0 wt %; particulate bone in an amount of from about 20.0%v/v to about 90.0%v/v; water in an amount of from about 20.0%v/v to about 90.0%v/v; and optionally containing one or more pharmaceutically active agents.

4. A bone matrix composition, consisting essentially of: one or more non-liquid cellulosics; particulate bone; and water.

5. The composition of claim 4, wherein said one or more non-liquid cellulosics are present in an amount of from 0.1 wt % to about 9.0 wt %.

6. The composition of claim 4, said one or more non-liquid cellulosics are selected from the group consisting of: carboxy methyl cellulose, hydroxy propyl cellulose; hydroxy ethyl cellulose; and methyl cellulose.

7. The composition of any one of claims 1, 2, 3, or 4, said particulate bone comprising one or members selected from the group consisting of: allogenic bone and xenogenic bone.

8. The composition of claim 7, said particulate bone comprising one or members selected from the group consisting of: demineralized cortical bone, demineralized cancellous bone, demineralized corticocancellous bone, non-demineralized cortical bone, non-demineralized cancellous bone, non-demineralized corticocancellous bone, partially demineralized cortical bone, partially demineralized cancellous bone, and partially demineralized corticocancellous bone.

9. The composition of claim 3, said one or more non-liquid members selected from the group consisting of: carboxy methyl cellulose, hydroxy propyl cellulose; hydroxy ethyl cellulose; and methyl cellulose, is present in an amount of from about 0.1 wt % to about 9.0 wt %; particulate bone is present in an amount of from about 35.0%v/v to about 65.0%v/v; and water is present in an amount of from about 30.0%v/v to about 70.0%v/v.

10. A bone matrix composition, consisting essentially of: one or more non-liquid members selected from the group consisting of: carboxy methyl cellulose, hydroxy propyl cellulose; hydroxy ethyl cellulose; and methyl cellulose; particulate bone; water, and optionally one or more pharmaceutically active agents, produced by the process comprising: mixing said particulate bone with said one or more non-liquid members selected from the group consisting of carboxy methyl cellulose, hydroxy propyl cellulose; hydroxy ethyl cellulose; and methyl cellulose, to produce a non-liquid particulate mixture; and mixing said water with said non-liquid particulate mixture to form said composition.

11. A solid composition, consisting essentially of: one or more non-liquid members selected from the group consisting of: carboxy methyl cellulose, hydroxy propyl cellulose; hydroxy ethyl cellulose; and methyl cellulose; particulate bone; water, and optionally one or more pharmaceutically active agents, produced by the process comprising:

combining said particulate bone with said one or more non-liquid members selected from the group consisting of carboxy methyl cellulose, hydroxy propyl cellulose; hydroxy ethyl cellulose; and methyl cellulose, to produce a non-liquid particulate mixture;

mixing said water with said non-liquid particulate mixture to form a matrix composition, and removing water from said matrix composition to form said solid composition, wherein said one or more pharmaceutically active agents are optionally added during any one or more of said steps of combining and mixing.

12. The solid composition of claim 11, said step of removing comprising freeze-drying.

13. The solid composition of claim 11, said process further comprising: performing any one or more of said steps of combining, mixing, and removing, under positive or negative pressure.

14. A method for producing a solid composition, comprising:
   combining particulate bone with one or more non-liquid members selected from the group consisting of carboxy methyl cellulose, hydroxy propyl cellulose; hydroxy ethyl cellulose; and methyl cellulose, to produce a non-liquid particulate mixture;
   mixing water with said non-liquid particulate mixture to form a matrix composition, and
   removing water from said matrix composition to form said solid composition.

15. The method of claim 14, said step of removing comprising freeze-drying.

16. The method of claim 14, further comprising: mixing said non-liquid particulate mixture and/or said matrix composition, with one or more pharmaceutically active agents prior to removing.

17. A method for producing a bone matrix composition, comprising:
   combining particulate bone with one or more non-liquid members selected from the group consisting of carboxy methyl cellulose, hydroxy propyl cellulose; hydroxy ethyl cellulose; and methyl cellulose, to produce a non-liquid particulate mixture; and
   mixing water with said non-liquid particulate mixture to form said bone matrix composition.

18. The method of claim 17, further comprising: mixing said non-liquid particulate mixture and/or said bone matrix composition, with one or more pharmaceutically active agents.

19. A bone matrix composition, consisting essentially of: one or more non-liquid members selected from the group consisting of: carboxy methyl cellulose, hydroxy propyl cellulose; hydroxy ethyl cellulose; and methyl cellulose; particulate bone; water, and optionally one or more pharmaceutically active agents, produced by the process comprising:
   combining said particulate bone with said one or more non-liquid members selected from the group consisting of carboxy methyl cellulose, hydroxy propyl cellulose; hydroxy ethyl cellulose; and methyl cellulose, to produce a non-liquid particulate mixture; and
   mixing said water with said non-liquid particulate mixture to form a bone matrix composition, wherein said one or more pharmaceutically active agents are optionally added during any one or more of said steps of combining and mixing.

20. A bone matrix composition, consisting essentially of: one or more non-liquid semi-synthetic polymers in an amount of from 0.1 wt % to 9.0 wt %; particulate bone; water, and optionally one or more pharmaceutically active agents, produced by the process comprising:
   combining said particulate bone with said one or more non-liquid cellulosics to produce a non-liquid particulate mixture; and
   mixing said water with said non-liquid particulate mixture to form a bone matrix composition, wherein said one or more pharmaceutically active agents are optionally added during any one or more of said steps of combining and mixing.

21. A bone matrix composition, consisting essentially of: one or more non-liquid members selected from the group consisting of: carboxy methyl cellulose, hydroxy propyl cellulose; hydroxy ethyl cellulose; and methyl cellulose, in an amount of from 0.1 wt % to 9.0 wt %; particulate bone; water, and optionally one or more pharmaceutically active agents.

22. A bone matrix composition, consisting essentially of: carboxy methyl cellulose in an amount of from 0.1 wt % to 9.0 wt %; particulate bone; water, and optionally one or more pharmaceutically active agents.

23. A bone matrix composition, consisting essentially of: one or more non-liquid semi-synthetic polymers in an amount of from 0.1 wt % to 9.0 wt %; particulate bone; water, and optionally one or more pharmaceutically active agents.

24. The composition of any one of claims 20 or 23, wherein said one or more non-liquid semi-synthetic polymers comprise one or more water-soluble, non-liquid, semi-synthetic polymers.

25. The composition of any one of claims 2, 3, 11, 21, 22, or 23, said one or more pharmaceutically active agents comprise bone marrow cells.

26. The composition of any one of claims 2, 3, 11, 21, 22, or 23, said one or more pharmaceutically active agents comprise one or more angiogenic factors.

27. A bone matrix composition, consisting essentially of: one or more non-liquid members selected from the group consisting of: methyl cellulose, carboxy methyl cellulose, hydroxy propyl cellulose, and hydroxy ethyl cellulose; particulate bone; water; and one or more angiogenic factors selected from the group consisting of nicotine and nicotinic acid.

28. A bone matrix composition, consisting essentially of: one or more non-liquid members selected from the group consisting of: methyl cellulose, carboxy methyl cellulose, hydroxy propyl cellulose, and hydroxy ethyl cellulose, in an amount of from about 0.1 wt % to about 9.0 wt %; particulate bone in an amount of from about 20.0%v/v to about 90.0%v/v; water in an amount from about 20.0%v/v to about 90%v/v; and optionally containing one or more angiogenic factors selected from the group consisting of nicotine and nicotinic acid.

29. A solid composition, consisting essentially of one: or more non-liquid members selected from the group consisting of: carboxy methyl cellulose, hydroxy propyl cellulose, hydroxy ethyl cellulose, and methyl cellulose; particulate bone; water; and optionally one or more one or more angiogenic factors selected from the group consisting of nicotine and nicotinic acid, produced by the process comprising:
   combining said particulate bone with said one or more non-liquid members selected from the group consisting of carboxy methyl cellulose, hydroxy propyl cellulose, hydroxy ethyl cellulose, and methyl cellulose, to produce a non-liquid particulate mixture;
   mixing said water with said non-liquid particulate mixture to form a matrix composition, and
   removing water from said matrix composition to form said solid composition,
      wherein said one or more angiogenic factors are optionally added during any one or more of said steps of combining and mixing.

30. A bone matrix composition, consisting essentially of: one or more non-liquid members selected from the group consisting of: carboxy methyl cellulose, hydroxy propyl cellulose, hydroxy ethyl cellulose, and methyl cellulose, in an amount of from 0.1 wt % to 9.0 wt %; particulate bone; water, and optionally one or more one or more angiogenic factors selected from the group consisting of nicotine and nicotinic acid.

31. A bone matrix composition, consisting essentially of: carboxy methyl cellulose in an amount of from 0.1 wt % to 9.0 wt %; particulate bone; water, and optionally one or more angiogenic factors selected from the group consisting of nicotine and nicotinic acid.

32. A bone matrix composition, consisting essentially of: one or more non-liquid semi-synthetic polymers in an amount of from 0.1 wt % to 90 wt %; particulate bone; water, and optionally one or more angiogenic factors selected from the group consisting of nicotine and nicotinic acid.

33. The bone matrix composition of any one of claims 1–6, 9–22, or 23, said particulate bone consists of: non-demineralized particulate bone, and optionally one or more members selected from the group consisting of partially demineralized particulate bone and demineralized particulate bone.

34. The bone matrix composition of claim 8, said particulate bone consists of non-demineralized particulate bone, and optionally one or more members selected from the group consisting of partially demineralized particulate bone and demineralized particulate bone.

35. The bone matrix composition of claim 8, said particulate bone consists of: non-demineralized particulate bone, and optionally one or more members selected from the group consisting of partially demineralized particulate bone and demineralized particulate bone.

36. A bone matrix composition, consisting of: one or more non-liquid members selected from the group consisting of: methyl cellulose, carboxy methyl cellulose, hydroxy propyl cellulose, and hydroxy ethyl cellulose; particulate bone; and water.

37. A bone matrix composition, consisting of: one or more non-liquid members selected from the group consisting of: methyl cellulose, carboxy methyl cellulose, hydroxy propyl cellulose, and hydroxy ethyl cellulose; particulate bone; water; and one or more angiogenic factors selected from the group consisting of nicotine and nicotinic acid.

38. A bone matrix composition, consisting of: one or more non-liquid members selected from the group consisting of: methyl cellulose, carboxy methyl cellulose, hydroxy propyl cellulose, and hydroxy ethyl cellulose, in an amount of from about 0.1 wt % to about 90.0 wt %; particulate bone in an amount of from about 20.0%v/v to about 90.0%v/v; water in an amount from about 20.0%v/v to about 90%v/v; and optionally containing one or more angiogenic factors selected from the group consisting of nicotine and nicotinic acid.

39. A solid composition, consisting of: one or more non-liquid members selected from the group consisting of: carboxy methyl cellulose, hydroxy propyl cellulose, hydroxy ethyl cellulose, and methyl cellulose; particulate bone; water; and optionally one or more one or more angiogenic factors selected from the group consisting of nicotine and nicotinic acid, produced by the process comprising:

combining said particulate bone with said one or more non-liquid members selected from the group consisting of carboxy methyl cellulose, hydroxy propyl cellulose, hydroxy ethyl cellulose, and ethyl cellulose, to produce a non-liquid particulate mixture, mixing said water with said non-liquid particulate mixture to form a matrix composition, and removing water from said matrix composition to form said solid composition,
wherein said one or more angiogenic factors are optionally added during any one or more of said steps of combining and mixing.

40. A bone matrix composition, consisting of: one or more non-liquid members selected from the group consisting of: carboxy methyl cellulose, hydroxy propyl cellulose, hydroxy ethyl cellulose, and methyl cellulose, in an amount of from 0.1 wt % to 9.0 wt %; particulate bone; water, and optionally one or more one or more angiogenic factors selected from the group consisting of nicotine and nicotinic acid.

41. A bone matrix composition, consisting of: carboxy methyl cellulose in an amount of from 0.1 wt % to 9.0 wt %; particulate bone; water, and optionally one or more angiogenic factors selected from the group consisting of nicotine and nicotinic acid.

42. A bone matrix composition, consisting of: one or more non-liquid semi-synthetic polymers in an amount of from 0.1 wt % to 9.0 wt %; particulate bone; water, and optionally one or more angiogenic factors selected from the group consisting of nicotine and nicotinic acid.

43. The bone matrix composition of any one of claims 1–6, 9–10, 19–23, 36–38, 40–41 or 42, said particulate bone consists of dry bone.

44. The bone matrix composition of claim 8, said particulate bone consists of dry bone.

* * * * *